(12) United States Patent
Xie et al.

(10) Patent No.: US 9,395,452 B2
(45) Date of Patent: Jul. 19, 2016

(54) MULTILAYER SCINTILATION CRYSTAL AND PET DETECTOR

(71) Applicant: RAYCAN TECHNOLOGY CO., LTD, Suzhou (CN)

(72) Inventors: Qingguo Xie, Suzhou (CN); Daoming Xi, Suzhou (CN); Jun Zhu, Suzhou (CN); Luyao Wang, Suzhou (CN)

(73) Assignee: Raycan Technology Co., Ltd., Suzhou (CN)

( * ) Notice: Subject to any disclaimer, the term of this patent is extended or adjusted under 35 U.S.C. 154(b) by 0 days.

(21) Appl. No.: 14/409,513

(22) PCT Filed: Mar. 4, 2013

(86) PCT No.: PCT/CN2013/072127
§ 371 (c)(1),
(2) Date: Dec. 19, 2014

(87) PCT Pub. No.: WO2013/189188
PCT Pub. Date: Dec. 27, 2013

(65) Prior Publication Data
US 2015/0323684 A1   Nov. 12, 2015

(30) Foreign Application Priority Data
Jun. 21, 2012  (CN) .......................... 2012 1 0207766

(51) Int. Cl.
*G01T 1/20* (2006.01)
*G01T 1/202* (2006.01)
(Continued)

(52) U.S. Cl.
CPC ............... *G01T 1/202* (2013.01); *A61B 6/4258* (2013.01); *G01T 1/1642* (2013.01);
(Continued)

(58) Field of Classification Search
CPC ......... G01T 1/202; G01T 1/2002; G01T 1/20; G01T 3/06
See application file for complete search history.

(56) References Cited

U.S. PATENT DOCUMENTS

| 5,227,633 | A | 7/1993 | Ryuo et al. |
| 5,349,191 | A * | 9/1994 | Rogers ............... G01T 1/202 |
| | | | 250/363.02 |

(Continued)

FOREIGN PATENT DOCUMENTS

| CN | 1809762 A | 7/2006 |
| CN | 101806912 A | 8/2010 |

(Continued)

OTHER PUBLICATIONS

International Search Report of PCT/CN2013/072127.
(Continued)

*Primary Examiner* — Christine Sung
(74) *Attorney, Agent, or Firm* — Renner, Kenner; Arthur M. Reginelli

(57) ABSTRACT

A multilayer scintillation crystal (1) comprises n layers of array scintillation crystals and m layers of continuous scintillation crystals which have uncut inner parts, both n and m being integers greater than or equal to 1 and a sum of n and m being smaller than or equal to 10. The array scintillation crystals are formed by strip-type scintillation crystals arranged along the width and length directions, the array scintillation crystals and the continuous scintillation crystals are sequentially coupled along the height direction of the strip-type scintillation crystals to form the multilayer scintillation crystal (1), and the continuous scintillation crystals are located at the bottom of the multilayer scintillation crystal (1). The adding of the continuous scintillation crystals between the array scintillation crystals and a photoelectric detector system (2) facilitates photon diffusion of a scintillating light, and through optimization design of the thickness of the continuous scintillation crystals, the distribution of the scintillating light received by the photoelectric detector carries more abundant energy deposition information. More accurate energy deposition information of γ photons in the scintillation crystal can be obtained through full utilization of the abundant energy deposition information by using a corresponding information extraction algorithm.

10 Claims, 3 Drawing Sheets

(51) Int. Cl.
  *G01T 1/29* (2006.01)
  *A61B 6/00* (2006.01)
  *G01T 1/164* (2006.01)
  *G01T 3/06* (2006.01)

(52) U.S. Cl.
  CPC ............ *G01T 1/1644* (2013.01); *G01T 1/2002* (2013.01); *G01T 1/2985* (2013.01); *G01T 1/20* (2013.01); *G01T 3/06* (2013.01)

(56) References Cited

U.S. PATENT DOCUMENTS

| | | | | |
|---|---|---|---|---|
| 5,453,623 | A * | 9/1995 | Wong | G01T 1/1642 250/363.03 |
| 5,594,253 | A | 1/1997 | Bueno et al. | |
| 6,087,665 | A | 7/2000 | Hoffman et al. | |
| 6,288,399 | B1 * | 9/2001 | Andreaco | G01T 1/1642 250/363.03 |
| 6,841,783 | B2 * | 1/2005 | Malmin | G01T 1/1644 250/363.03 |
| 7,087,905 | B2 * | 8/2006 | Murayama | G01T 1/2008 250/363.03 |
| 7,315,027 | B2 | 1/2008 | Okada et al. | |
| 7,601,963 | B2 * | 10/2009 | Aykac | G01T 1/202 250/367 |
| 7,709,801 | B2 * | 5/2010 | Ooi | G01T 1/1644 250/361 R |
| 8,436,312 | B2 * | 5/2013 | Inadama | G01T 1/1644 250/332 |
| 2009/0159804 | A1 * | 6/2009 | Shibuya | G01T 1/2985 250/363.03 |
| 2010/0320389 | A1 | 12/2010 | Tonami et al. | |
| 2012/0049075 | A1 | 3/2012 | Nariyuki | |
| 2013/0299707 | A1 * | 11/2013 | Levin | G01T 1/164 250/363.03 |
| 2014/0209804 | A1 * | 7/2014 | Lee | G01T 1/2008 250/362 |

FOREIGN PATENT DOCUMENTS

| | | |
|---|---|---|
| CN | 101925834 A | 12/2010 |
| CN | 102707310 A | 10/2012 |
| JP | H04290983 A | 10/1992 |
| JP | H11326524 A | 11/1999 |
| JP | 20030255095 A | 9/2003 |
| JP | 2010204125 A | 9/2010 |

OTHER PUBLICATIONS

International Search Report dated May 6, 2013 of PCT/CN2013/072127.

Supplementary European Search Report dated Jun. 9, 2015 from Application No. EP 13807480.

JP Office Action dated Sep. 10, 2015 from corresponding JP Patent Appln No. 2015-517586.

English Translation of JP Office Action dated Sep. 10, 2015 from corresponding JP Patent Appln No. 2015-517586 (retrieved from Global Dossier System).

* cited by examiner

MULTILAYER SCINTILLATION CRYSTAL AND PET DETECTOR

The present application is a national stage application of International Application Ser. No. PCT/CN2013/072127, filed on Mar. 4, 2013, and claims the priority to Chinese Patent Application No. 201210207766.8, entitled "multilayer scintillation crystal and PET detector", filed on Jun. 21, 2012 with the State Intellectual Property Office of People's Republic of China, which is incorporated herein by reference in its entirety.

FIELD OF THE INVENTION

The present disclosure relates to the technical field of position emission tomography (PET) device, and in particular to a multilayer scintillation crystal and a PET detector in a PET device.

BACKGROUND

A PET detector, as a key component of a PET device, mainly functions to acquire position, time and energy information of energy deposition for each γ photon in a PET event. To improve imaging performance of PET system, it is desirable that the adopted PET detector can provide Depth of Interaction (DOI) information, high detection efficiency, good time resolution and good spatial resolution in designing and implementing.

A conventional PET detector usually uses a single-layer scintillation crystal array or a single-layer continuous scintillation crystal as its scintillation crystal portion. For such a PET detector using a single-layer scintillation crystal array, the spatial resolution is determined by the size of the strip-type crystals in the scintillation crystal array. If a Silicon Photomultiplier (be abbreviated as SiPM) (or an Avalanche Photo Diode, hereafter APD) array is used as a photoelectric converter, the size of the strip-type crystal could not be too small, or else scintillating light output by several strip-type crystals will be received by a same SiPM (or APD) in a SiPM array (or an APD array), which finally leads to a result that the energy deposition position of γ photons could not be distinguished. For a PET detector using a single-layer continuous scintillation crystal, scintillating light which is caused by energy deposition of γ photons in the single-layer continuous scintillation crystal diffuses into a specific spatial distribution. The energy deposition position of the γ photons can be calculated based on the spatial distribution of the scintillating light detected by a photoelectric detector, but in order to accurately calculate the energy deposition position of the γ photons in the crystal and improve the spatial resolution of the detector, a large mount of reference data is needed to acquire critical system parameters (Joung, Jinhun; Miyaoka, R. S. Robert S.; Lewellen, T. K. Thomas K., "cMiCE: a high resolution animal PET using continuous LSO with a statistics based positioning scheme", Nuclear instruments & methods in physics research, Section A, Accelerators, spectrometers, detectors and associated equipment, Volume: 489, pp. 584-598, 2002). The acquisition of the reference data is time-consuming and laborious, which determines that this kind of detector cannot be mass produced or be applied in a clinic PET system.

It is found promising to design a high performance PET detector by using a multilayer scintillation crystal. At present, the multilayer scintillation crystal is mainly adopted to acquire DOI information, and the scintillation crystal directly coupled to a photoelectric detector is always scintillation crystal array. Schmand M. et al design a PET detector with double-layers crystal array by using two types of scintillation crystals with different decay times, to acquire DOI information of energy deposition for γ photons in the PET detector (Schmand, M.; Eriksson, L.; Casey, M. E.; Andreaco, M. S.; Melcher, C.; Wienhard, K.; Flugge, G; Nutt, R., "Performance results of a new DOI detector block for a high resolution PET-LSO research tomography HRRT", Nuclear Science, IEEE Transactions on, Volume:45, Issue:6, pp. 3000-3006, 1998). More energy deposition information of γ photons in the scintillation crystal can be acquired by designing a PET detector with a multilayer crystal.

Hence, to solve the technical problems in the conventional PET detector using a single-layer crystal, it is necessary to provide a multilayer scintillation crystal with novel structure to overcome shortcomings of the conventional PET detector.

SUMMARY

In view of this, the purpose of this disclosure is to provide a multilayer scintillation crystal, which allows distribution of scintillating light received by a photoelectric detector to carry more abundant energy deposition information.

In order to realize above purpose, the technical solution of the disclosure is as follows:

A multilayer scintillation crystal includes n layers of scintillation crystal array and m layers of continuous scintillation crystals which are not cut internally, both n and m are integers greater than or equal to 1, a sum of m and n is smaller than or equal to 10, the scintillation crystal array are built by strip-type scintillation crystals arranged along width and length directions, the scintillation crystal array and the continuous scintillation crystals are orderly coupled along a height direction of the strip-type scintillation crystals to form the multilayer scintillation crystal, and the bottom layer of the multilayer scintillation crystal is continuous scintillation crystal.

Preferably, in the multilayer scintillation crystal, n and m are both equal to 1, the multilayer scintillation crystal includes a bottom scintillation crystal layer and a top scintillation crystal layer, wherein the bottom scintillation crystal layer is the continuous scintillation crystal, the top scintillation crystal layer is the scintillation crystal array, and the top scintillation crystal layer includes a top surface used as an incident plane of γ photons.

Preferably, in the multilayer scintillation crystal, the height for the top scintillation crystal layer ranges from 5 mm to 15 mm when the height for the bottom scintillation crystal layer ranges from 0.1 mm to 10 mm.

Preferably, in the multilayer scintillation crystal, the height for the top scintillation crystal layer ranges from 0.1 mm to 10 mm when the height for the bottom scintillation crystal layer ranges from 4 mm to 15 mm.

Preferably, in the multilayer scintillation crystal, m is greater than or equal to 2, the multilayer scintillation crystal includes a bottom scintillation crystal layer, a top scintillation crystal layer opposite to the bottom scintillation crystal layer, and a middle scintillation crystal layer between the top scintillation crystal layer and the bottom scintillation crystal layer, wherein, the bottom scintillation crystal layer is continuous scintillation crystal, the top scintillation crystal layer is continuous scintillation crystal or scintillation crystal array, the middle scintillation crystal layer includes h layers of scintillation crystal array and p layers of continuous scintillation crystals, in the case where the top scintillation crystal layer is formed by the continuous scintillation crystal, h equals to n and p equals to m−2; in the case where the top scintillation crystal layer is formed by the scintillation crystal array, h equals to n−1 and p equals to m−1, the top scintillation crystal layer includes a top surface used as an incident plane of γ photons.

Preferably, in the multilayer scintillation crystal, the height for the top scintillation crystal layer ranges from 0.1 mm to 10 mm when the height for the bottom scintillation crystal layer ranges from 0.1 mm to 10 mm, the sum height of h layers of scintillation crystal array and n layers of continuous scintillation crystals ranges from 1 mm to 15 mm, where the h layers of scintillation crystal array and the n layers of continuous scintillation crystals are located between the top scintillation crystal layer and the bottom scintillation crystal layer in the multilayer scintillation crystal.

Preferably, in the multilayer scintillation crystal, a coupler is disposed between joint surfaces of two jointing layers of scintillation crystals in the multilayer scintillation crystal to couple the two layers of scintillations crystals.

Preferably, in the multilayer scintillation crystal, the coupler is optical glue or a light guide or glass or an optical element.

Preferably, in the multilayer scintillation crystal, any scintillation crystal layer in the multilayer scintillation crystal is formed by an inorganic scintillation crystal.

A PET detector includes the multilayer scintillation crystal as described above.

It may be seen from above technical solution, according to the disclosure, the multilayer scintillation crystal includes continuous scintillation crystals disposed between a photoelectric detector and a scintillation crystal array. The adding of the continuous scintillation crystals facilitates diffusion of scintillating light photons, and allows scintillating light distribution carrying more abundant energy deposition information by optimizing the thickness of the continuous scintillation crystals. More accurate energy deposition information of γ photons in the scintillation crystal can be obtained through full utilization of the abundant energy deposition information by applying a corresponding information extraction algorithm.

BRIEF DESCRIPTION OF THE DRAWINGS

To describe the technical solutions according to the embodiments of the present disclosure or conventional technology more clearly, in the following the drawings involved in the embodiments of the present disclosure or in the conventional technology are described. Apparently, the drawings described below are only some of the embodiments, and persons of ordinary skill in the art can derive other drawings according to the drawings without any creative effort.

Figure 1:
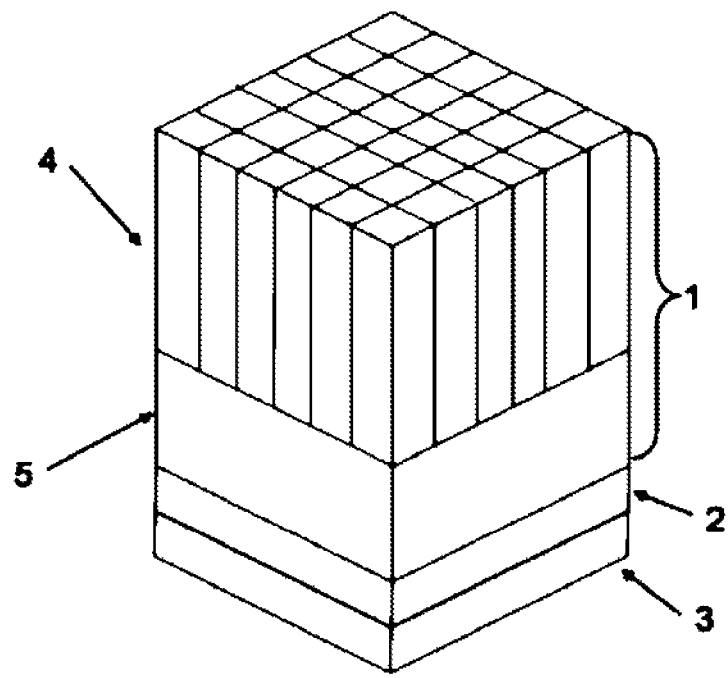
FIG. 1 is a schematic diagram of a PET detector according to the first embodiment of the disclosure.

1 denotes a multilayer scintillation crystal; 2 denotes a photoelectric detector system; 3 denotes an algorithm system; 4 denotes a top scintillation crystal layer; 5 denotes a bottom scintillation crystal layer; 6 denotes a light guide; 7 denotes a middle scintillation crystal layer.

DETAILED DESCRIPTION

A PET detector using the multilayer crystal may obtain more energy deposition information of γ photons in the scintillation crystal. In a conventional multilayer scintillation crystal, scintillation crystal coupled to a photoelectric detector system is scintillation crystal array. Nevertheless, adding a continuous scintillation crystal, which is coupled between the scintillation crystal array and the photoelectric detector system, facilitates the diffusion of scintillating light photons, and allows scintillating light distribution received by the photoelectric detector carrying more abundant energy deposition information by optimizing the thickness of the continuous scintillation crystal. More accurate energy deposition information of γ photons in the scintillation crystal can be obtained through full utilization of the abundant energy deposition information by applying a corresponding information extraction algorithm.

Based on above analysis, the present disclosure discloses a multilayer scintillation crystal, which is formed by stacking at least one scintillation crystal array and at least one continuous scintillation crystal in the direction perpendicular to a horizontal plane.

Specifically, a multilayer scintillation crystal includes n layers of scintillation crystal array and m layers of continuous scintillation crystals which are not cut internally. n and m are both integers greater than or equal to 1. The sum of m and n is smaller than or equal to 10. The scintillation crystal array is formed by strip-type scintillation crystals arranged along width and length directions of the scintillation crystal array. The scintillation crystal array and the continuous scintillation crystals are coupled orderly along height direction of the strip-type scintillation crystals to form the multilayer scintillation crystal, and a continuous scintillation crystal forms the bottom layer of the multilayer scintillation crystal.

In the case where n and m are both equal to 1, the multilayer scintillation crystal includes a bottom scintillation crystal layer and a top scintillation crystal layer opposite to the bottom scintillation crystal layer. The bottom scintillation crystal layer is formed by the continuous scintillation crystal, and the top scintillation crystal layer is formed by the scintillation crystal array. The top scintillation crystal layer includes a top surface used as an incident plane of γ photons. In the case where the height for the top scintillation crystal layer ranges from 5 mm to 15 mm, the height for the bottom scintillation crystal layer ranges from 0.1 mm to 10 mm. In the case where the height for the top scintillation crystal layer ranges from 0.1 mm to 10 mm, the height for the bottom scintillation crystal layer ranges from 4 mm to 15 mm.

In the case where m is greater than or equal to 2, the multilayer scintillation crystal includes a bottom scintillation crystal layer, a top scintillation crystal layer opposite to the bottom scintillation crystal layer, and a middle scintillation crystal layer located between the top scintillation crystal layer and the bottom scintillation crystal layer. The bottom scintillation crystal layer is formed by a continuous scintillation crystal, and the top scintillation crystal layer is formed by a continuous scintillation crystal or a scintillation crystal array. The middle scintillation crystal layer includes h layers of scintillation crystal array and p layers of continuous scintillation crystals; in the case where the top scintillation crystal layer is formed by a continuous scintillation crystal, h equals to n and p equals to m−2; in the case where the top scintillation crystal layer is formed by a scintillation crystal array, h equals to n−1 and p equals to m−1. The top scintillation crystal layer includes a top surface used as an incident plane of γ photons. The height for the top scintillation crystal layer ranges from 0.1 mm to 10 mm while the height for the bottom scintillation crystal layer ranges from 0.1 mm to 10 mm, and the sum of the heights of the h layers of scintillation crystal array and the p layers of continuous scintillation crystals ranges from 1 mm to 15 mm, where the h layers of scintillation crystal array and the p layers of continuous scintillation crystals are located between the top scintillation crystal layer and the bottom scintillation crystal layer in the multilayer scintillation crystal.

With reference to FIG. 1 to FIG. 6, in the multilayer scintillation crystal according to the disclosure, the upper surface of a diagram is defined as a top surface, the lower surface of the diagram is defined as a bottom surface, the highest layer of the diagram is defined as a top layer, and the lowest layer of the diagram is defined as a bottom layer.

According to the disclosure, any scintillation crystal layer in the multilayer scintillation crystal may be formed by an inorganic scintillation crystal, which may be made from bismuth germanium oxide, lutetium oxyorthosilicate, lutetium-yttrium oxyorthosilicate, yttrium silicate, barium fluoride, sodium iodide, cesium iodide, lead tungstate, or lanthanum bromide.

The multilayer scintillation crystal according to the disclosure includes continuous scintillation crystals disposed between a photoelectric detector and a scintillation crystal array and disposed between the crystal arrays. The adding of the continuous scintillation crystals facilitates diffusion of scintillating light photons, and allows scintillating light distribution received by the photoelectric detector carrying more abundant energy deposition information through an optimized design of the thickness of the continuous scintillation crystals. More accurate energy deposition information of γ photons in the scintillation crystal can be obtained through full utilization of the abundant energy deposition information by applying a corresponding information extraction algorithm.

The disclosure further discloses a PET detector, which includes the foregoing multilayer scintillation crystal for converting γ photons into scintillating light. The PET detector of this structure may acquire position and time information of γ photons energy deposition in the scintillation crystal with higher accuracy and γ photon detection efficiency. The PET detector further includes a photoelectric detector system for converting the scintillating light into an electric signal, and an algorithm system for acquiring magnitude, position and time of energy deposition for the γ photons in the multilayer scintillation crystal according to the electric signal.

The bottom layer of the multilayer scintillation crystal is formed by a continuous scintillation crystal, where the bottom surface of the continuous scintillation crystal is coupled to the photoelectric detection surface of the photoelectric detector system via optical glue or a light guide or glass or other optical element. A coupler is disposed between joint surfaces of two jointing layers of scintillation crystals in the multilayer scintillation crystal, to couple to the two layers of scintillation crystals, where the coupler is optical glue or a light guide or glass or an optical element.

The photoelectric detector system may be a Position Sensitive PhotoMultiplier Tubes (hereafter PSPMT), or a Micro Channel Plates (hereafter MCP), or an array of c×d avalanche photo diodes (hereafter APDs) arranged in a horizontal plane, or an array of c×d silicon photomultipliers (here after SiPMs)) arranged in the horizontal plane, or an array of c×d photomultiplier tubes (here after PMTs)) arranged in the horizontal plane, where c, being an integer greater or equal to 1, represents the number of SiPMs (or APDs or PMTs) in a length direction of the horizontal plane, d, being an integer greater or equal to 1, represents the number of SiPMs (or APDs or PMTs) in a width direction of the horizontal plane, and c and d is not equal to 1 at the same time. For one event of energy deposition of γ photons, k electric pulse signals may be generated by the photoelectric detector system, where the k is an integer greater or equal to 2.

The algorithm system may calculate the energy deposition position of γ photons in the multilayer scintillation crystal according to the k electrical pulse signals by using a position algorithm, where the position algorithm includes center of gravity algorithm, Anger-Logic algorithm, maximum likelihood estimate algorithm, and statistical-based locating algorithm, three-dimensional nonlinear locating algorithm, and artificial neural network locating algorithm.

The algorithm system may calculate the time of γ photons energy deposition in the multilayer scintillation crystal according to the k electrical pulse signals by using a time algorithm, where an additive electric pulse signal "sum" is acquired by adding all of the k electric pulse signals, and the time information, indicating the energy deposition time of the γ photons in the multilayer scintillation crystal, is extracted from the addictive electric pulse signal. The addition of the electric pulses is done by adding k electric pulses directly in time domain or adding k electric pulses in different weights in time domain.

Alternatively, the algorithm system may calculate the energy deposition time of γ photons in the multilayer scintillation crystal according to the k electrical pulse signals through using another time algorithm, where in the time algorithm, k pieces of time information are extracted respectively according to the k electric pulse signals and the energy deposition time of the γ photons in the multilayer scintillation crystal is estimated according to these k pieces of time information. The process for estimating energy deposition time of the γ photons in the multilayer scintillation crystal according to the k time points includes: calculating an average of the k time periods, calculating a minimum of the k time periods, or calculating a maximum likelihood value of the k time periods.

In the following, the description of the disclosure is made with reference to drawings of several embodiments of the disclosure. Apparently, the described embodiments are merely a few rather than all of the embodiments of the present disclosure. All other embodiments obtained by those of ordinary skills in the art based on the embodiment of the present disclosure without creative efforts shall fall within the scope of the present disclosure.

The First Embodiment

As shown in FIG. 1, a PET detector includes a multilayer scintillation crystal 1, a photoelectric detector system 2, and an algorithm system 3. The multilayer scintillation crystal is formed by two layers of scintillation crystals, where the top scintillation crystal layer 4 is formed by a scintillation crystal array, the bottom scintillation crystal layer 5 is formed by a continuous scintillation crystal, and the joint surfaces of these two layers of scintillation crystals are coupled together via optical glue. The top scintillation crystal layer 4, which is in a shape of a cube, is formed by 6×6 strip-type scintillation crystals in same size arranged in the horizontal plane. The bottom surface of the bottom scintillation crystal layer 5 is directly coupled to the photoelectric detector system 2. The photoelectric detector system 2 is formed by a 4×4 SiPM array. The height of bottom scintillation crystal layer 5 is 1 mm, and the height of top scintillation crystal layer 4 is 13 mm. The algorithm system uses Anger-Logic algorithm for acquiring energy deposition position of γ photons. The algorithm system extracts time information from the added signal, which is obtained by adding the outputs of the 4×4 SiPMs, as the energy deposition time of γ photons.

The Second Embodiment

Figure 2:
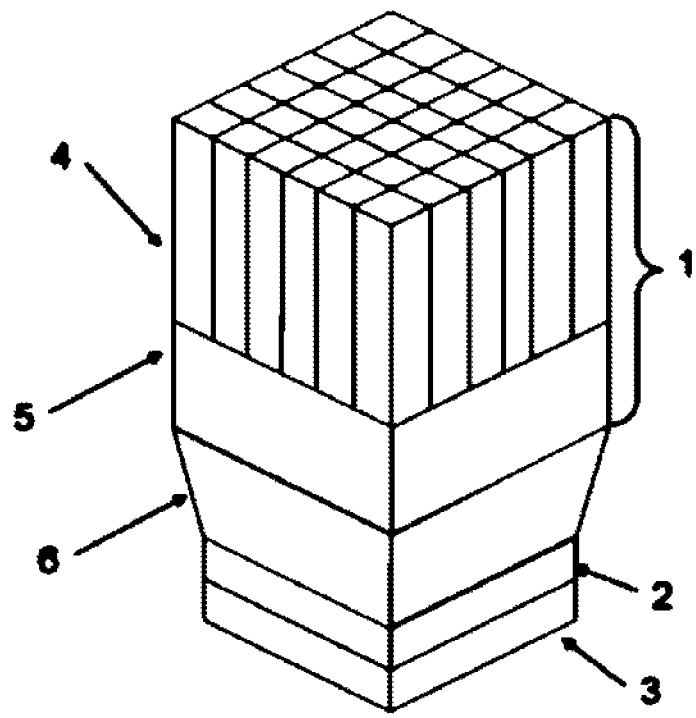
FIG. 2 is a schematic diagram of a PET detector according to the second embodiment of the disclosure.

As shown in FIG. 2, a PET detector includes a multilayer scintillation crystal 1, a photoelectric detector system 2, and an algorithm system 3. The multilayer scintillation crystal 1 is formed by two layers of scintillation crystals, where the top scintillation crystal layer 4 is formed by a scintillation crystal array, the bottom scintillation crystal layer 5 is formed by a continuous scintillation crystal, and the joint surfaces of the two layers of scintillation crystals, which have exactly same shapes and sizes, are coupled together via optical glue. The top scintillation crystal layer 4, which is in a shape of a cube, is formed by 6×6 strip-type scintillation crystals in same size arranged in the horizontal plane. The bottom surface of the bottom scintillation crystal layer 5 is coupled to the photoelectric detector system 2 via a light guide 6. The photoelectric detector system 2 is formed by a 4×4 SiPM array. The height of bottom scintillation crystal layer 5 is 1 mm, and the height of top scintillation crystal layer 4 is 13 mm. The algorithm system uses Anger-Logic algorithm for acquiring energy deposition position of γ photons. The algorithm system extracts time information from the added signal, which is obtained by adding the outputs of the 4×4 SiPMs, as the energy deposition time of γ photons.

The Third Embodiment

Figure 3:
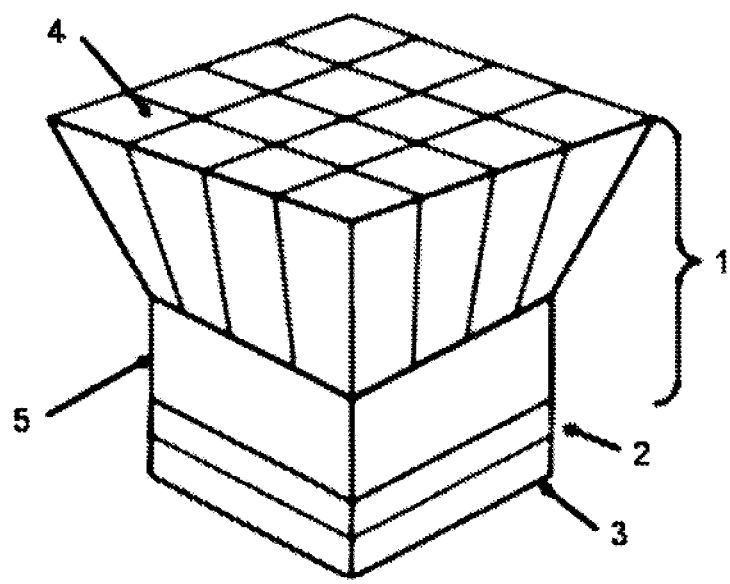
FIG. 3 is a schematic diagram of a PET detector according to the third embodiment of the disclosure.

As shown in FIG. 3, a PET detector includes a multilayer scintillation crystal 1, a photoelectric detector system 2, and an algorithm system 3. The multilayer scintillation crystal is formed by two layers of scintillation crystals, where the top scintillation crystal layer 4 is formed by a scintillation crystal array, the bottom scintillation crystal layer 5 is formed by a continuous scintillation crystal, and the joint surfaces of the two layers of scintillation crystals are coupled together via optical glue. The top scintillation crystal layer 4 is in a shape of a frustum, for which a top surface and a bottom surface are parallel to each other. The top scintillation crystal layer 4 is formed by 4×4 strip-type scintillation crystals arranged in a horizontal plane. The bottom surface of the bottom scintillation crystal layer 5 is coupled to the photoelectric detector system 2 via optical glue. The height of bottom scintillation crystal layer 5 is 1 mm, and the height of top scintillation crystal layer 4 is 13 mm. The photoelectric detector system 2 is formed by a 4×4 SiPM array. The algorithm system 3 uses Anger-Logic algorithm for acquiring energy deposition position of γ photons. The algorithm system 3 extracts time information from the added signal, which is obtained by adding the outputs of the 4×4 SiPMs, as the energy deposition time of γ photons.

The Fourth Embodiment

Figure 4:
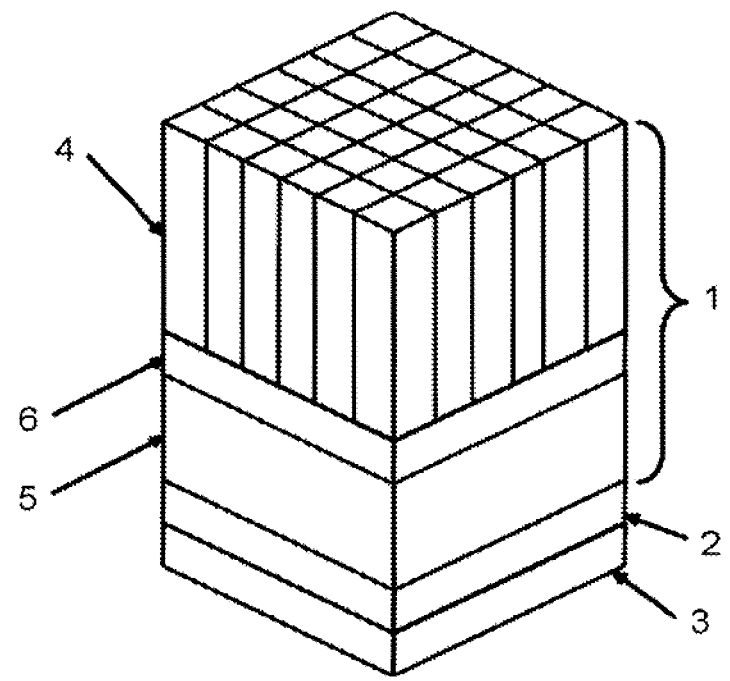
FIG. 4 is a schematic diagram of a PET detector according to the fourth embodiment of the disclosure.

As shown in FIG. 4, a PET detector includes a multilayer scintillation crystal 1, a photoelectric detector system 2, and an algorithm system 3. The multilayer scintillation crystal is formed by two layers of scintillation crystals, where the top scintillation crystal layer 4 is formed by a scintillation crystal array, the bottom scintillation crystal layer 5 is formed by a continuous scintillation crystal, and the joint surfaces of two layer of scintillation crystals, which have exactly same shapes and sizes, are coupled together via a light guide 6. The top scintillation crystal layer 4, which is in a shape of a cube, is formed by 6×6 strip-type scintillation crystals in same size arranged in the horizontal plane. The bottom surface of the bottom scintillation crystal layer 5 is coupled to the photoelectric detector system 2 via optical glue. The photoelectric detector system 2 is formed by a 4×4 SiPM array. The height of bottom scintillation crystal layer 5 is 1 mm, and the height of top scintillation crystal layer 4 is 13 mm. The algorithm system 3 uses Anger-Logic algorithm for acquiring energy deposition position of γ photons. The algorithm system 3 extracts time information from the added signal, which is obtained by adding the outputs of the 4×4 SiPMs, as the energy deposition time of γ photons.

The Fifth Embodiment

Figure 5:
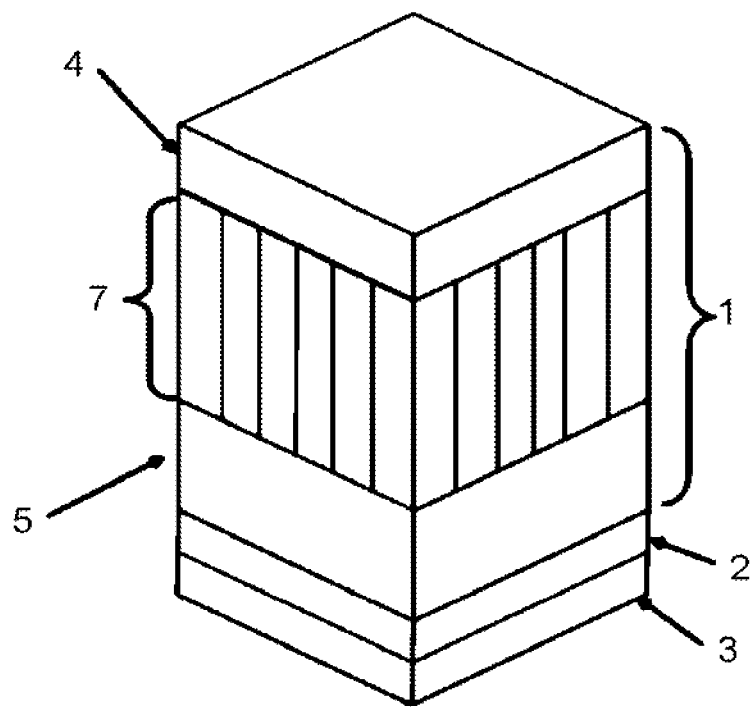
FIG. 5 is a schematic diagram of a PET detector according to the fifth embodiment of the disclosure.

As shown in FIG. 5, a PET detector includes a multilayer scintillation crystal 1, a photoelectric detector system 2, and an algorithm system 3, where the multilayer scintillation crystal 1 is formed by three layers of scintillation crystals, including one layer of scintillation crystal array and two layers of continuous scintillation crystals. Both of the top scintillation crystal layer 4 and the bottom scintillation crystal layer 5 are formed by a continuous scintillation crystal. A middle scintillation crystal layer 7 between the top scintillation crystal layer 4 and the bottom scintillation crystal layer 5, is formed by a scintillation crystal array. The joint surfaces of the three layers of scintillation crystals are coupled via optical glue. The middle scintillation crystal layer 7 is formed by 6×6 strip-type scintillation crystals arranged in horizontal plane. The bottom surface of the bottom scintillation crystal layer 5 is coupled to the photoelectric detector system 2 via optical glue. The photoelectric detector system 2 is formed by a 4×4 SiPM array. The algorithm system 3 uses Anger-Logic algorithm for acquiring energy deposition position of γ photons. The algorithm system 3 extracts time information from the added signal, which is obtained by adding the outputs of the 4×4 SiPMs, as the energy deposition time of γ photons.

The Sixth Embodiment

Figure 6:
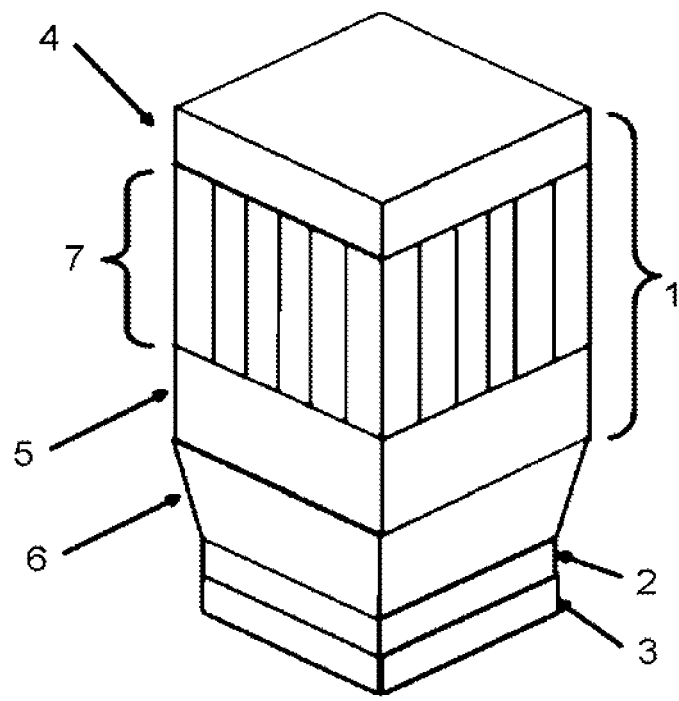
FIG. 6 is a schematic diagram of a PET detector according to the sixth embodiment of the disclosure; where

As shown in FIG. 6, a PET detector includes a multilayer scintillation crystal 1, a photoelectric detector system 2, and an algorithm system 3, where the multilayer scintillation crystal 1 is formed by three layers of scintillation crystals, including one layer of scintillation crystal array and two layers of continuous scintillation crystals. The top scintillation crystal layer 4 is formed by a continuous scintillation crystal, and the bottom scintillation crystal layer 5 is formed by a continuous scintillation crystal. A middle scintillation crystal layer 7 between the top scintillation crystal layer 4 and the bottom scintillation crystal layer 5, is formed by a scintillation crystal array. The joint surfaces of the three layers of scintillation crystals are coupled via optical glue. The middle scintillation crystal layer 7 is formed by 6×6 strip-type scintillation crystals arranged in horizontal plane. The bottom surface of the bottom scintillation crystal layer 5 is coupled to the photoelectric detector system 2 via a light guide 6. The photoelectric detector system 2 is formed by a 4×4 SiPM array. The algorithm system 3 uses Anger-Logic algorithm for acquiring energy deposition position of γ photons; the algorithm system 3 extracts time information from the added signal, which is obtained by adding the outputs of the 4×4 SiPMs, as the energy deposition time of γ photons.

Those of ordinary skills in the art will appreciate that the disclosure is not limited to the details of above exemplary embodiments and may be realized with other specific forms without departing from the spirit and basic features of the disclosure. Hence, the embodiments should be considered in any case as exemplary rather than limiting, and the scope of the disclosure is defined by the claims but not the above description. Therefore, the disclosure is meant to include all changes within the contents and equivalence of the claims. The reference numerals in the claims should not be seen as a limitation to the claims.

In addition, it should be understood that although the specification is described with reference to several embodiments, not every embodiment forms an independent technical solution. The arrangement of the specification is merely for purpose of clarity. Those of ordinary skills in the art should take the specification as a whole, and technical solutions in the embodiments may be properly combined to form other understandable embodiments.

What is claimed is:

1. A multilayer scintillation crystal comprising:
n layer(s) of scintillation crystal array and
m layer(s) of continuous scintillation crystals,
wherein each layer of the continuous scintillation crystals is not cut internally, both n and m are integers greater than or equal to 1, the sum of m and n is smaller than or equal to 10,
each layer of the scintillation crystal array is formed by strip-type scintillation crystals arranged along width and length directions of the scintillation crystal array,
each layer of the scintillation crystal array and each layer of the continuous scintillation crystals are orderly coupled along a height direction of the strip-type scintillation crystals to form the multilayer scintillation crystal, and
a bottom layer of the multilayer scintillation crystal is a layer of the continuous scintillation crystal.

2. The multilayer scintillation crystal according to claim 1, wherein n and m are both equal to 1, the multilayer scintillation crystal comprises a bottom scintillation crystal layer and a top scintillation crystal layer opposite to the bottom scintillation crystal layer, the bottom scintillation crystal layer is formed by a layer of continuous scintillation crystals, the top scintillation crystal layer is formed by a layer of scintillation crystal array, and the top scintillation crystal layer comprises a top surface used as an incident plane of γ photons.

3. The multilayer scintillation crystal according to claim 2, wherein a height for the top scintillation crystal layer ranges from 5 mm to 15 mm, and a height for the bottom scintillation crystal layer ranges from 0.1 mm to 10 mm.

4. The multilayer scintillation crystal according to claim 2, wherein a height of top scintillation crystal layer ranges from 0.1 mm to 10 mm, and a height of bottom scintillation crystal layer ranges from 4 mm to 15 mm.

5. The multilayer scintillation crystal according to claim 1, wherein m is greater than or equal to 2, the multilayer scintillation crystal comprises a bottom scintillation crystal layer, a top scintillation crystal layer opposite to the bottom scintillation crystal layer, and a middle scintillation crystal layer located between the top scintillation crystal layer and the bottom scintillation crystal layer, wherein the bottom scintillation crystal layer is formed by a layer of continuous scintillation crystals, the top scintillation crystal layer is formed by a layer of continuous scintillation crystals or the scintillation crystal array, the middle scintillation crystal layer comprises h layers of scintillation crystal array and p layers of continuous scintillation crystals, in the case where the top scintillation crystal layer is formed by a layer of continuous scintillation crystals, h equals to n and p equals to m−2, while in the case where the top scintillation crystals layer is formed by a scintillation crystal array, h equals to n−1 and p equals to m−1, the top scintillation crystal layer comprises a top surface used as an incident plane of γ photons.

6. The multilayer scintillation crystal according to claim 5, wherein the height of top scintillation crystal layer ranges from 0.1 mm to 10 mm, the height of bottom scintillation crystal layer ranges from 0.1 mm to 10 mm, and the sum heights of the h layers of scintillation crystal array and the n layers of continuous scintillation crystals ranges from 1 mm to 15 mm, where the h layers of scintillation crystal array and the n layers of continuous scintillation crystals are located between the top scintillation crystal layer and the bottom scintillation crystal layer in the multilayer scintillation crystal.

7. The multilayer scintillation crystal according to claim 1, wherein a coupler is disposed between joint surfaces of two jointing layers of scintillation crystals in the multilayer scintillation crystal to couple the two layers of scintillations crystals.

8. The multilayer scintillation crystal according to claim 7, wherein the coupler is optical glue or a light guide or glass or other optical elements.

9. The multilayer scintillation crystal according to claim 1, wherein any scintillation crystal layer in the multilayer scintillation crystal is formed by an inorganic scintillation crystal.

10. A PET detector comprising the multilayer scintillation crystal according to claim 1.

* * * * *